(12) United States Patent
Helmer et al.

(10) Patent No.: US 8,395,014 B2
(45) Date of Patent: Mar. 12, 2013

(54) MOISTURE MONITOR SYSTEM FOR DIAPERS AND ALIKE

(75) Inventors: Richard James Neil Helmer, Victoria (AU); Michael Anthony Mestrovic, Victoria (AU); Pamela Margaret Petersen, Victoria (AU)

(73) Assignee: Commonwealth Scientific and Industrial Research Organisation, Campbell Act (AU)

( * ) Notice: Subject to any disclaimer, the term of this patent is extended or adjusted under 35 U.S.C. 154(b) by 1005 days.

(21) Appl. No.: 12/278,058

(22) PCT Filed: Jan. 31, 2007

(86) PCT No.: PCT/AU2007/000086
§ 371 (c)(1),
(2), (4) Date: Dec. 8, 2008

(87) PCT Pub. No.: WO2007/087674
PCT Pub. Date: Aug. 9, 2007

(65) Prior Publication Data
US 2009/0292265 A1 Nov. 26, 2009

(30) Foreign Application Priority Data
Feb. 1, 2006 (AU) .................. 2006900483

(51) Int. Cl.
*A61F 13/15* (2006.01)
(52) U.S. Cl. ..... 604/361; 604/374; 604/378; 340/573.5; 340/604; 340/605
(58) Field of Classification Search .................. 604/361, 604/374, 378; 340/573.5, 572.1, 573.1, 604, 340/605, 602
See application file for complete search history.

(56) References Cited

U.S. PATENT DOCUMENTS

| 5,645,542 | A | * | 7/1997 | Anjur et al. | 604/368 |
|---|---|---|---|---|---|
| 5,820,973 | A | * | 10/1998 | Dodge et al. | 428/212 |
| 5,959,535 | A | * | 9/1999 | Remsburg | 340/604 |
| 6,097,297 | A | | 8/2000 | Fard | |
| 6,362,389 | B1 | * | 3/2002 | McDowall et al. | 604/367 |
| 7,649,125 | B2 | * | 1/2010 | Ales et al. | 604/361 |
| 2004/0064114 | A1 | | 4/2004 | David et al. | |

FOREIGN PATENT DOCUMENTS

| JP | 2001-095831 A | 4/2001 |
|---|---|---|
| JP | 2005-052564 A | 3/2005 |
| WO | 99/25247 A1 | 5/1999 |

* cited by examiner

*Primary Examiner* — Tatyana Zalukaeva
*Assistant Examiner* — Benedict L Hanrahan
(74) *Attorney, Agent, or Firm* — Sughrue Mion, PLLC

(57) ABSTRACT

The present invention relates to a system suitable for monitoring multiple leakage events such as wetting of a diaper or alike sanitary product. The system includes two or more than two electrodes that are supported in a spaced apart relationship and a liquid permeable substrate between the electrodes that lacks or has a low capacity for holding or storing liquid. In the event of liquid leakage, an electrical bridge connecting the electrodes can be formed by the liquid, and before the product becomes saturated liquid can freely drain from the permeable substrate and disconnect the electrodes. Upon further liquid leakage, electrical connection between the electrodes can be reformed indicating multiple liquid leakage events. In the situation where the sanitary product becomes saturated and liquid is prevented from draining from the permeable substrate, the electrical connection will continue, indicating that the sanitary product requires changing.

24 Claims, 4 Drawing Sheets

MOISTURE MONITOR SYSTEM FOR DIAPERS AND ALIKE

CROSS REFERENCE TO RELATED APPLICATIONS

This application is a National Stage of International Application No. PCT/AU2007/000086 filed Jan. 31, 2007, claiming priority based on Australian Patent Application No. 2006900483 filed Feb. 1, 2006, the contents of all of which are incorporated herein by reference in their entirety.

FIELD AND BACKGROUND OF THE INVENTION

The present invention relates to a moisture monitoring system that can be used to monitor wetting of garments, diapers, nappies, incontinence pads and alike sanitary products.

Generally speaking modern disposable diapers and nappies are designed so as to include a hydrophobic lining that faces or contacts a wearer's skin and a hydrophilic core or reservoir for storing liquid. During use, the vast majority of liquid is drawn through the hydrophobic lining to the hydrophilic core so that the wearer feels dry and comfortable. When the capacity of the hydrophilic core is exceeded, liquid ceases to be wicked away from the hydrophobic lining and the wearer will inevitably beginning to feel wet and uncomfortable.

Incontinence often manifests as periodic leakage of relatively small amounts of urine and the reservoirs of modern disposable diapers and pads are capable of absorbing a series of leakages before it requires changing.

In the case of incontinent elderly or disabled patients that have been admitted to caring facilities such as nursing homes, a major duty of the staff of the caring facility is to determine when a diaper or pad requires changing. It is standard practice for this to be carried out by staff manually inspecting the wetness of diapers and pads on a routine basis. However, this type of acute patient management is labour intensive and may create some embarrassment for the patient.

It is an object of the present invention to enable the staff of a caring facility to monitor the wetness of a diaper without carrying out manual inspection that is now standard practice.

SUMMARY OF THE INVENTION

According to the present invention there is provided a moisture monitoring system suitable for monitoring liquid leakage of a wearer and, in turn, for monitoring wetting of a diaper, nappy, incontinence pad or alike sanitary product. The system includes:

a) two or more than two electrodes each being supported in a spaced apart relationship; and b) a liquid permeable substrate between the electrodes, the liquid permeable substrate lacking or having a low capacity for holding or storing liquid, whereby in the event of initial liquid leakage, an electrical bridge connecting the electrodes extends, at least in part, through the permeable substrate by liquid located on or therein, and subsequently liquid can drain from the permeable substrate so as to electrically disconnect the electrodes, and upon further liquid leakage, electrical connection between the electrodes can be reformed.

An advantage of the present invention is that the liquid permeable substrate enables liquid forming the electrical connection between the electrodes to freely drain such that the electrical connection is only temporary or for a period that is commensurate to the amount of liquid leakage. In addition, in the event of further leakage the electrical connection can be reformed. This enables a caring facility to monitor the frequency of multiple leakage incidents without manually inspecting the sanitary product.

The permeable substrate may extend continuously between the electrodes from one electrode to another. Alternatively, the substrate may have one or more intermittent gaps between the electrodes so as to extend between the electrodes in a discontinuous manner. The gaps may be left unoccupied or they may be at least partially filled with other material such as a hydrophobic polypropylene material.

According to one embodiment, it is preferred that the liquid permeable substrate be in direct contact with at least one and possibly both electrodes.

It is preferred that the liquid permeable layer have passageways or openings that allow liquid to freely flow there through, the passageways or openings having a diameter or cross-section in the range of 0.05 to 10.0 mm, and suitably from 0.5 to 10.0 mm.

It is preferred that the liquid permeable layer have passageways or openings of a size ranging from 1.0 to 5.0 mm.

It is even more preferred that the passageways or openings be in the size range of 1.0 to 3.0 mm.

It is preferred that the liquid permeable layer has a thickness in the range of 2.0 to 10.0 mm.

It is preferred that the liquid permeable layer be hydrophobic.

The liquid permeable layer may be rendered hydrophobic by any one or a combination of the following hydrophobic agents: fluorocarbons, hydrocarbons, silicones and waxes. Examples of commercial hydrophobic agents include Rucostar EEE by Rudolf Chemie, SM8709 by Dow Corning/Toray and Nuva TTC by Clariant.

It is preferred that the liquid permeable layer be a low density polymeric material. For example, the liquid permeable layer may be made from, but is by no means limited to, any one or a combination of the following materials: polyurethane, polyester, polystyrene, polypropylene or polyethylene. Physical or surface treatments such as plasma or corona discharges may also be used for rendering materials, such as polyester hydrophobic.

It is preferred that the system further include a liquid absorbing substrate having a higher capacity for holding or storing liquid than the liquid permeable substrate, wherein liquid in the permeable substrate can drain into the absorbing substrate, and in the event of liquid leakage, the electrical bridge connecting the electrodes is formed by liquid located solely in the permeable substrate or by liquid located in the permeable substrate and the absorbing substrate. In other words, depending on the extent to which liquid has drained from the permeable substrate, the electrical bridge, or path of least electrical resistance may be formed from liquid contained entirely in the permeable substrate or by a continuous path of liquid in the permeable and absorbing substrates.

It is preferred that the absorbing substrate be in direct contact with the liquid permeable substrate.

In the event that the storage capacity of the absorbing substrate has been reached, liquid will cease to be wicked into the absorbing substrate and in which case, the electrodes will remain in electrical connection by virtue of liquid retained in the liquid permeable substrate. In other words, it is preferred that when the storage capacity of the absorbing substrate has been reached or is unable to continue absorbing liquid, drainage of liquid from the liquid permeable layer will be hampered and thus electrical connection between the electrodes will be maintained. In the situation where the system is being used to monitor the wetness of a diaper or alike sanitary product and the electrical connection between the electrodes continues after a reasonable period has lapsed to allow the liquid to drain, it is probable that the wearer of the diaper or sanitary product is beginning to feel wet and uncomfortable.

It is even more preferred that the absorbing substrate be a cotton scrim or tissue.

It is preferred that the absorbing substrate be hydrophilic. The absorbing substrate may be made from any suitable absorbent material and may in addition to fibrous material include absorbent gels, crystals, and emulsions.

It is preferred that the electrodes be spatially separated from the absorbing substrate.

It is preferred that each electrode be supported by, or be in direct contact with a text substrate with the liquid permeable layer located between the textile substrates. Preferably, one of the substrates is capable of wicking liquid.

Although the textile substrates may include various types of fibres and may be of any form, it is preferred that the textile substrates contain cellulosic fibres. It is also preferred that the textile substrates have a thin tissue configuration in which the fibres are randomly configured.

According to one preferred embodiment the textile substrate is hydrophobic, and according to another preferred embodiment the textile substrate is hydrophilic.

It is preferred that the textile substrates include one or more than one layers of a polyethylene non-woven fabric or scrim.

Although it is possible that the textile substrates in contact with the electrodes may be spatially separated over distances and by various layers of material, it is preferred that the liquid permeable layer be the only layer between the textile substrates.

Although it is possible that the electrodes may be in any physical configuration including a sheet, panel or some form of netting or lattice structure, it is preferred that the electrodes have an elongate structure.

It is even more preferred that the electrodes be a ribbon, thread or strand.

The electrodes of the system may be provided according to two alternative forms that will now be described in detail. According to one preferred form, the electrodes are made of dissimilar materials and when liquid leakage occurs, the liquid and oxygen create an oxidising environment that can be utilised to generate an electrical current by way of a redox type reaction. In this situation, it is preferred that the electrodes form part of electrolytic cell wherein one of the electrodes is a sacrificial metal containing anode and the other electrode is an inert cathode such that when exposed to leakage, the liquid forms an electrolytic bridge between the electrodes allowing a redox type reaction in which reduction of oxygen occurs at the cathode and oxidation of a metal occurs at the anode. The redox reactions can generate an electrical current between the electrodes which can be measured using suitable devices.

Ideally, both the anode and cathode would have the properties of the anodes and cathodes described in our co-pending International application PCT/AU2006/001793 entitled A WATER ACTIVATED SYSTEM INCLUDING A FLEXIBLE SUBSTRATE which claims priority from provisional application 2006900483. The patent specifications of the provisional and International applications are hereby incorporated into this specification by express reference.

Generally speaking it is preferred that the sacrificial anode contain any one or more of the following metals aluminium, cooper, tin, iron, zinc or silver and the cathode be directly or indirectly coupled to the anode.

The cathode may be made of any suitable inert material such as conductive plastic or an inert metal substrate such as silver wire. Similarly, the cathode may include filament or staple fibres and the surface of the fibre include an inert conductive material. The fibre included in the cathode may be any natural or synthetic fibre including: proteinaceous fibres such as wool, hair and fur; cellulosic fibres such as cotton, linen and hemp; and synthetic fibres such as nylon, polyesters, polypropylene and polyamides. The inert conductive material included in the cathode may be any suitable material including any one or a combination of conductive polymers such as pedot, polyacetylene, polypyrrole and polyaniline or conductive inks such as carbon ink and silver ink.

The anode may be in any suitable form including but by no means limited to: foils, wires, fibres or a flexible substrate on which the metal has been applied. For example, the substrate may be coated with a metal by conventional spraying, direct contact, printing, or other vapour or chemical deposition techniques. Ideally, the anode contains aluminium or an aluminium containing alloy.

According to a second alternative form of the electrodes, it is preferred that the electrodes be made from substantially inert conductive material and that electrical connection between the electrodes be measured by monitoring changes in electrical resistance or conductivity between the electrodes.

It is preferred that the electrodes be made from materials having the same electro potential.

It is preferred that the electrodes be made entirely or at least in part from textile conductive materials including but by no means limited to yarns, threads, strands, filaments, fabrics, films and foils.

It is preferred that the electrodes be made entirely or at least in part from any one or a combination of monofilaments such as metal coated synthetic filaments, conductive carbon monofilaments, and conductive polymers such as pedot, polyacetylene, polypyrrole and polyaniline.

It is even more preferred that the electrodes be a nylon thread with a silver coating.

In the event that the storage capacity of the absorbing substrate has been reached, drainage of liquid from the liquid permeable layer will be hampered and thus electrical connection with be maintained. In the situation where the system is being used to monitor the wetness of a diaper or alike sanitary product and the electrical connection between the electrodes is not disconnected after a reasonable period, it is probable that the wearer of the diaper or sanity product is beginning to feel wet and uncomfortable.

In the situation when the electrodes are in the form of a flexible conductive textile, the electrodes may be incorporated into the textile substrate by way of any suitable means including laminating methods, sewing, knitting, weaving or by insertion of the electrode in the textile substrate during the manufacture thereof.

In the situation where the textile substrate has a plurality of layers, it is preferred that the electrodes be positioned between the layers.

It is preferred that the textile substrate also have electrical conductive properties when wet. An advantage provided by this feature is that when the substrate is wet the active sensory area of the electrodes is equivalent to the area of the textile substrate.

It is preferred that the system also include a means for producing an output in response to electrical connection or disconnection between the electrodes. In other words, changes in electrical conductivity between the electrodes. The output may be an audio, visual or electromagnetic signal.

For example, the output means may include transmitters and receivers that interact by way of electromagnetic signals. Moreover, the output means may have suitable logic maintained in memory devices such as USB keys and other writeable and rewritable memory devices.

In the situations where the system is used to monitor the wetness of a diaper or alike sanitary product and liquid is prevented from draining from the liquid permeable substrate the output means produces an output indicating that the diaper or sanitary product requires replacing.

It is preferred that the system include a means for recording electrical connection or conductivity, or changes thereof between the electrodes. The recording means may be used to record incidences of leakage events which can then be used to evaluate the wetness of a diaper and when it requires changing.

According to the present invention there is provided a system including:

a) two or more than two electrodes each being supported by a textile substrate in a spaced apart relationship, each textile substrate being capable of wicking liquid; and b) a liquid permeable layer positioned between the textile substrates, the liquid permeable layer lacking or having a low capacity for holding or storing liquid, whereby in the event of initial liquid leakage, liquid in contact with at least one of the textile substrates can be drawn through the substrates and pass through the permeable layer so as to form an electrical connection between the electrodes, subsequently liquid can drain from the permeable layer so as to electrically disconnect the electrodes, and upon further liquid leakage, electrical connection between the electrodes can be reformed.

According to the present invention there is also provided a system including:

a) two or more than two electrodes each being supported in a spaced apart relationship;

b) a liquid permeable substrate located between the electrodes, the liquid permeable substrate lacking or having a low capacity for holding or storing liquid; and c) an liquid absorbing substrate in contact with the liquid permeable substrate, the liquid absorbing substrate having a higher capacity for holding or storing liquid;

whereby in the event of initial liquid leakage, the liquid can bridge and make electrical connection with the electrodes as the liquid passes through the permeable substrate to the liquid absorbing substrate, and upon liquid draining from the permeable substrate and being absorbed by the absorbing substrate the electrical bridge between the electrodes can be disconnected, and wherein upon further liquid leakage the liquid bridge and electrical connection between the electrodes can be reformed.

The embodiments of the present invention mentioned in the two preceding paragraphs may also include any one or a combination of the following features:

features relating to the electrodes, namely whether the electrodes form part of electrolytic cell in which one is a cathode and the other is a anode or, alternatively, the electrodes are substantially inert yet conductive and an external power source is coupled to the electrodes so that changes in electrical resistance between the electrodes is able to be measured;

features of the liquid permeable substrate; and features pertaining to the textile wicking substrate.

According to the present invention there is also provided a diaper, nappy or alike sanitary product including the system either with or without any one or a combination of the preferred features thereof mentioned in the preceding paragraphs.

According to the present invention there is also provided a garment or undergarment including the system either with or without any one or a combination of the preferred features thereof mentioned in the preceding paragraphs. This embodiment of the present invention may be used to monitor other forms of wetting other than urinal leakage such as, but by no means limited to, sweat, and may even be used to monitor wetness from external sources such as rainwater.

BRIEF DESCRIPTION OF THE DRAWINGS

Three preferred embodiments will now be described with reference to the accompanying drawings, of which.

DETAILED DESCRIPTION

The embodiments of the invention shown in the Figures are described below in the context of monitoring the wetness of diapers or other sanitary products. However, it will be appreciated that the present invention can be used in various other applications such as monitoring the frequency of discharge of sweat or monitoring wetness caused by rainwater.

Figure 1:
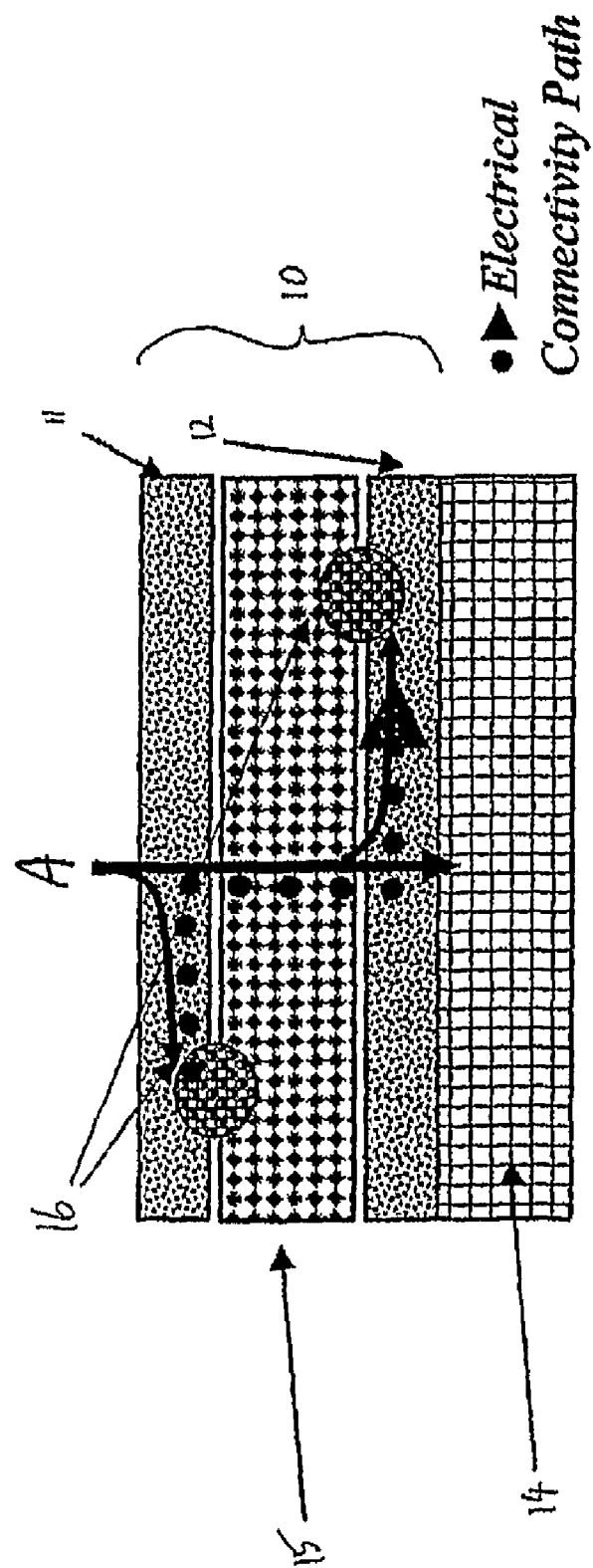
FIG. 1 is cross-sectional view of a three layered panel according to a first embodiment of the present invention, the panel being positioned adjacent to an absorptive core of a conventional diaper and is equipped with a system for monitoring wetness.

With respect to the embodiment shown in FIG. 1, the panel 10 includes two layers, namely upper and lower layers 11 and 12 respectively of a wicking textile material. Located below the panel 10 is a hydrophilic layer that is representative of a liquid absorbing core 14 of a diaper. The core 14 may in fact be a multilayered structure or have the structure of any conventional diaper. Preferably, layers 11 and 12 are hydrophobic in comparison to the hydrophilic core 14 and are made from a polypropylene scrim. In the situation where the panel 10 is incorporated in a diaper, the layers 11 and 12 can be positioned immediately adjacent to the hydrophilic core 14 and indeed, may be integrally formed with the liquid reservoir of a diaper. Alternatively, the panel 10 can be separate and independent of a diaper and in which case, the panel 10 may be a separate item that is located in the crouch region of any diaper or pad as desired.

Located between the textile layers 11 and 12 is a porous liquid permeable layer 15. The porous layer 15 does not have any, or only very little liquid holding properties and, therefore, is a layer through which liquid can readily drain. Ideally, the porous layer 15 is a low density polyurethane foam material having openings or passageways through which liquid can drain. The passageways may be in any geometric shape but preferably have a diameter of at least 0.5 mm so that liquid can freely drain therethrough.

Located on the inner face of each wicking textile layer 11 and 12 is a conductive yarn 16, preferably in the form of a silver coated nylon thread or yarn such as Shieldex™ 125/17 (2 ply). The yarn 16 may be any yarn that is essentially an inert conductive yarn.

The arrows in FIG. 1 show the directions in which liquid in contact with the upper textile layer 11 passes through the panel 10. Specifically, liquid discharged above the panel at point A is able to be wicked through the upper layer 11 and make contact with the electrode of the upper layer 16. Simultaneously, liquid is able to pass through the porous layer 15 and wick through the lower textile layer 12 so as to make contact with the electrode 16 of the lower layer 12 and thereby make a complete electrical connection between the electrodes. Typically the line of dots between the electrodes illustrates the path of least electrical resistance when liquid is discharged from position A.

As liquid drains from the upper textile layer 11, the porous layer 15 and to some extent the upper and lower textile layers 11 and 12 will dry. As this occurs the path of least electrical resistance will change and the conductivity between the electrodes will dissipate.

It is possible for the electrical conductivity between the electrodes to be measured by at least two alternative methods. The first involves using the liquid leakage as an electrolyte and requires the electrodes to be made from difference electro potential materials such that the electrodes form anodes and cathodes of an electrolytic cell.

The second method and the more preferred method will now be described with reference to the text results shown in FIG. 2. Specifically, it is preferred that the electrodes have the same electro potential such as the Shieldex™ 125/17 silver coated nylon threads. The electrodes are coupled to the external power source which supplies an electrical potential and/or current to the electrodes. Liquid leakage reduces electrical resistance between the electrodes which can be measured using suitable electronics voltage and current meters and logic.

Although not shown in the drawings, the voltage and current meters or logic devices may be directly connected to electrodes using any suitable means such as conductive adhesive tape, conductive clips or conductive Velcro™.

Figure 2:
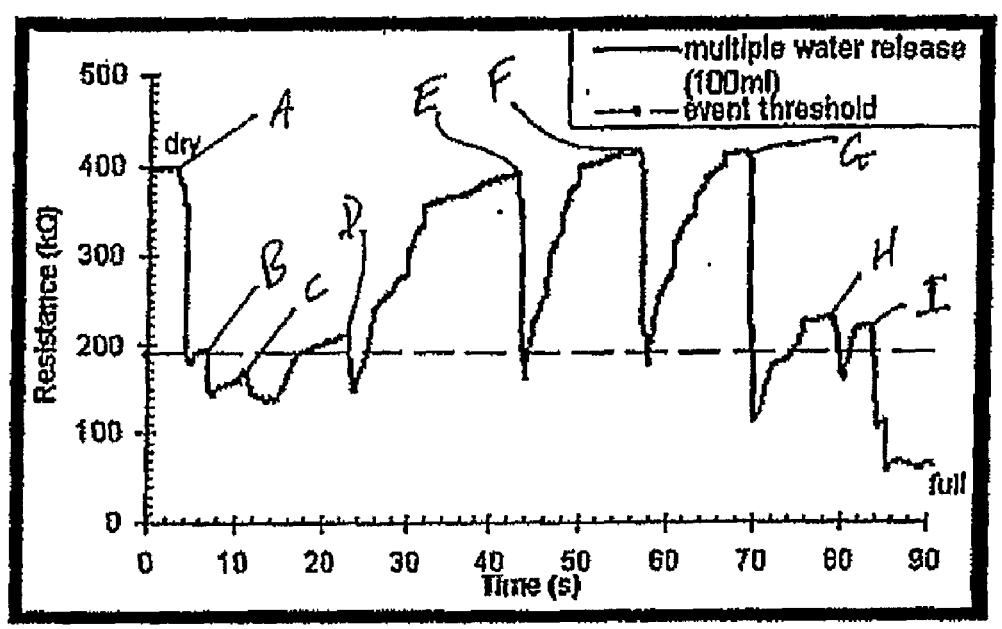
FIG. 2 is a graph illustrating the changes in electrical conductivity measured between two electrodes of the panel shown in FIG. 1 during a 90 second trial involving the release of 100 ml of water.

FIG. 2 illustrates the results of a trial in which 100 ml of water was released onto the panel located on an absorptive hydrophilic core in accordance with the structure shown in FIG. 1. The water was released sporadically on a total of 9 occasions, each identified in the graph from A to I with the volume of water released on each occasion varying from 5 to 30 ml. FIG. 2 shows electrical resistance in kohms as a function of time. As can be seen, electrical resistance between the electrodes initially falls quickly after release of water indicating an increase in electrical conductivity and then resistance subsequently increases as the water drains from the porous layer into the absorptive core 14. After the release of water on the ninth occasion, identified in FIG. 2 by the letter I, the resistance remains low, thus indicating that high conductively is maintained between the electrodes. This occurs when the drainage of the liquid from the porous layer 15 is prevented by the absorptive core 14 being fully saturated and is unable to absorb any further liquid from the porous layer 15.

When the panel 10 is used in the manner shown in FIG. 2, staff of a caring facility has the ability to monitor the frequency of liquid leakage from a patient, monitor the wetness of a sanitary product and thus determine whether it requires changing, and monitor the quantity of liquid leaked on each occasion or over a period of time. Alternatively the voltage and/or current and/or resistance signals can be interpreted by logic located locally on the diaper or garment and/or remotely at a central monitoring station. The interpretation can be indicated locally on the diaper or garment electronic unit and/or remotely at a central monitoring station.

It is envisaged that the quantity of liquid leakage may be monitored as a function of: i) the period over which electrical connection or conductivity is measured; and ii) the number and size of the liquid passageways or openings in the liquid permeable layer 30. In other words the quantity of liquid leakage may be assessed in terms of the flow rate passing through the liquid passageways or openings.

Figure 3:
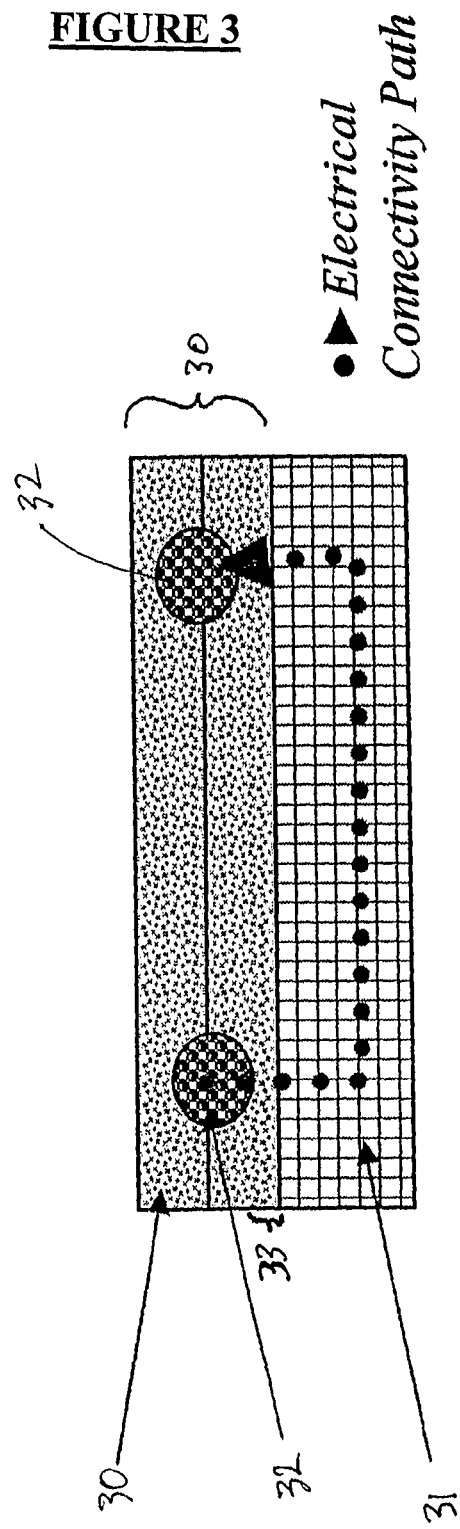
FIG. 3 is a cross-sectional view of a panel according to a second embodiment of the present invention, the panel being positioned adjacent to an absorptive core of a conventional diaper and is equipped with a system for monitoring the wetness.

The embodiment of the invention shown in FIG. 3 comprises: an upper hydrophobic layer 30 that is permeable to liquid by virtue of openings or liquid passageways which may preferably have a size ranging from 0.05 to 10.0 mm; a hydrophilic storage core 31; and two electrodes 32 that are spatially separated and supported above a section of the hydrophobic layer 30 at a spacing 33 from the hydrophilic core 31. The embodiment shown in FIG. 3 is representative of the basic structure of modern disposable diapers that have a hydrophilic storage core and a hydrophobic lining that contacts a wearer's skin.

In use, leakage of liquid from a wearer will be drawn to the storage core 31 through the hydrophobic layer 30. As the liquid is being drawn into the hydrophilic core 31, a continuous stream of the liquid in the hydrophobic layer may provide a path of least electrical resistance. However, as liquid is transferred into the hydrophilic core 31 and the amount of the liquid in the hydrophobic layer 30 diminishes, the path of least electrical resistance is more likely to be in the form of the dotted line shown in FIG. 3. Specifically, liquid absorbed by the hydrophilic core 31 will be disbursed therein by wicking and liquid remaining in the hydrophobic layer 30 together with liquid in the hydrophilic core 31 will provide an electrical connection between the electrodes. Upon further absorption of any residue liquid from the hydrophobic layer 30 into hydrophobic core 31, the electrical connection between the electrodes will be disconnected. When disconnection of the electrodes in this manner has been detected, a staff member of a caring facility can assume that the wearer feels relatively dry and comfortable.

If it is the case that the electrical connection is maintained after a reasonable time period has elapsed, the absorptive capacity of the hydrophilic core 31 may have been reached and, in turn, complete drainage of liquid from the hydrophobic layer 30 may be prevented. In this situation, the wearer of the diaper may begin to feel wet and uncomfortable and the staff of the caring facility can proceed to change the diaper or sanitary product.

It is preferred that the hydrophilic core 31 be made from cotton or tissue scrim and that the hydrophobic layer 30 comprise any one or a combination of: plaster type tape having openings of approximately 3 mm; low density foam having opening ranging from 0.5 to 10 mm in diameter; or material having irregular shaped openings commonly used as non-skid type material such as a material supplied by Ladelle Australian under the trade name "Grip It".

Figure 4:
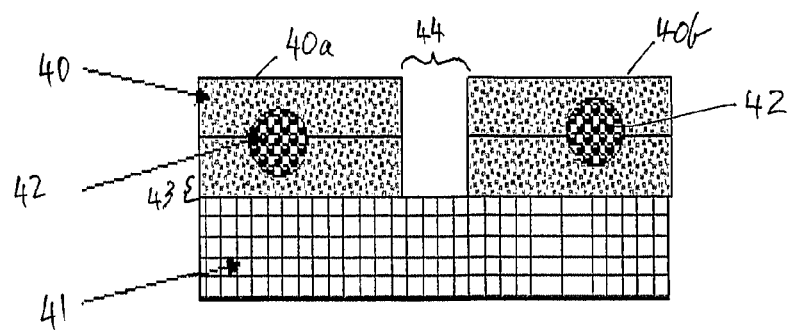
FIG. 4 is a cross-sectional view of a third embodiment of the present invention, the embodiment comprising panel sections positioned adjacent to an absorptive core and is equipped with a system for monitoring wetness.
Figure 5:
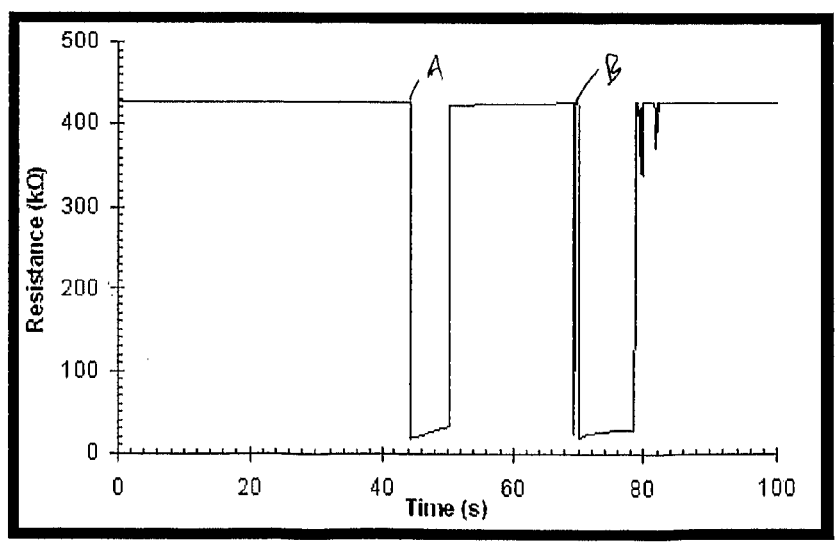
FIG. 5 is a graph illustrating changes in electrical conductivity measured between two electrodes of the embodiment shown in FIG. 4.

The embodiment shown in FIG. 4 is similar to the embodiment shown in FIG. 3 save for the panel 40 comprising separate sections 40a and 40b that are separated by a gap 44, and wherein each section contains an electrode 42. Each section 40a and 40b of the panel is hydrophobic and includes passageways or openings through which liquid can penetrate. Located below the panel 40 is a relatively hydrophilic core 41 that is akin to the absorptive core of a conventional diaper. As can be seen, the electrodes 42 are supported above the hydrophobic core 41 by a spacing 43. An advantage of the embodiment of FIG. 4 is that any electrical connection formed by residual liquid in the hydrophobic liquid porous layer is minimised. This advantage is illustrated by the results shown in FIG. 5 which demonstrate changes in electrical resistance. Specifically, FIG. 5 shows that when liquid is discharged the electrical resistance quickly reduces in response to liquid bridging between the electrodes and full electrical resistance is subsequently reinstated shortly thereafter when liquid in the gap has been absorbed by the core 41. Points A & B on FIG. 5 indicated when liquid has been discharged onto the panel.

Although not shown in FIG. 4 it is also possible for the gap 44 to be intermittently filled with a highly hydrophobic material such as polypropylene to create defined pores within the gap.

Those skilled in the art of the invention will appreciate that many modifications and variations may be made to the preferred embodiments described above without departing from the spirit and scope of the present invention.

The claims defining the invention are as follows:

1. A moisture monitoring system for monitoring liquid leakage of a wearer and, in turn, for monitoring wetting of a diaper, nappy, incontinence pad or alike sanitary product, the system including:
   i) two or more than two electrodes
   ii) a hydrophobic liquid permeable substrate in which the electrodes are encased and the liquid permeable substrate has one or more intermittent gaps between the electrodes so as to extend between the electrodes in a discontinuous manner, and wherein the liquid permeable substrate lacks or has a low capacity for holding or storing liquid; and
   iii) a hydrophilic liquid absorbing substrate in contact with the liquid permeable substrate,
   whereby in the event of any initial liquid leakage, an electrical bridge connecting the electrodes extends through the permeable substrate by liquid located on or in the permeable substrate only, said liquid subsequently drains from the permeable substrate so as to electrically disconnect the electrodes, and then following a further liquid leakage, another electrical bridge connecting the electrodes extending through the permeable substrate is reformed by liquid located on or in the permeable substrate only to enable multiple leakage events to the monitored, and
   wherein when the liquid storage capacity of the liquid absorbing substrate has been reached, drainage of the liquid from the liquid permeable substrate will be hampered and thus the electrodes will remain in electrical connection by virtue of liquid retained in the liquid permeable substrate.

2. The system according to claim 1, wherein the liquid permeable substrate has passageways or openings having a diameter or cross-section in the range of 0.05 to 10.0 mm that allow liquid to freely flow.

3. The system according to claim 1, wherein the liquid permeable substrate has passageways or openings having a diameter or cross-section in the size range of 0.5 to 5.0 mm.

4. The system according to claim 1, wherein the liquid permeable substrate has passageways or openings having a diameter or cross-section in the size range of 1.0 to 3.0 mm.

5. The system according to claim 1, wherein the liquid permeable substrate has a thickness in the range of 2 to 10 mm.

6. The system according to claim 1, wherein the liquid permeable substrates has been rendered hydrophobic by chemical treatment with any one or a combination of fluorocarbons, hydrocarbons, silicones, waxes, or by surface treatments involving the use of plasma or corona discharges.

7. The system according to claim 1, wherein the liquid permeable substrate is a low density polymeric material including any one or a combination of polyurethane, polyester, polystyrene, polypropylene and polyethylene.

8. The system according to claim 1, wherein the absorbing substrate is a cotton scrim or tissue.

9. The system according to claim 1, wherein the electrodes have an elongate structure such as a ribbon, thread or strand.

10. The system according to claim 1, wherein one of the electrodes is a sacrificial metal containing anode and the other electrode is an inert cathode such that when exposed to leakage, the liquid forms an electrolytic bridge between the electrodes allowing a redox type reaction in which reduction of oxygen occurs at the cathode and oxidation of a metal occurs at the anode.

11. The system according to claim 10, wherein the sacrificial anode contains any one or more of the following metals aluminium, cooper, tin, iron, zinc or silver and the cathode is directly or indirectly coupled to the anode.

12. The system according to claim 11, wherein the cathode includes a filament or staple fibre and the surface of the fibre includes an inert conductive material.

13. The system according to claim 12, wherein the inert conductive material is any one or a combination of depot, polyacetylene, polypyrrole, polyaniline, or conductive inks such as carbon ink and silver ink.

14. The system according to claim 11, wherein the anode is a foil, wire, fibre or a flexible substrate on which the metal has been applied.

15. The system according to claim 1, wherein the electrodes are made entirely or at least in part from substantially inert conductive material and electrical connection between the electrodes is measured by monitoring changes in electrical resistance or conductivity between the electrodes.

16. The system according to claim 15, wherein the electrodes are made entirely or at least in part from textile conductive materials including but by no means limited to yarns, threads, strands, filaments, fabrics, films or foils.

17. The system according to claim 16, wherein the electrodes are made entirely or at least in part from any one or a combination of monofilaments such as metal coated synthetic filaments, conductive carbon monofilaments, silver coated nylon, or conductive polymers such as polyacetylene, polypyrrole, polyaniline, or conductive inks such as carbon ink and silver ink.

18. The system according to claim 15, wherein the system includes a power source for applying an electrical potential difference and/or current to the electrodes and a means for determining changes in electrical resistance or conductivity between the electrodes.

19. The system according to claim 1, further including a means for producing an output in response to electrical connection or disconnection between the electrodes.

20. The system according to claim 19, wherein the output is an audio, visual or electromagnetic signal.

21. The system according to claim 19, wherein when the system is used to monitor the wetness of a diaper or alike sanitary product and liquid is prevented from draining from the liquid permeable substrate the output means produces an output indicating that the diaper or sanitary product requires replacing.

22. The system according to claim 1, wherein the system includes a means for recording electrical conductivity, connection, or changes thereof between the electrodes.

23. A diaper, nappy or alike sanitary product including the system according to claim 1.

24. A garment or undergarment including the system according to claim 1.

* * * * *